United States Patent
Ito

(10) Patent No.: US 6,503,389 B2
(45) Date of Patent: Jan. 7, 2003

(54) LIQUID CHROMATOGRAPH

(75) Inventor: Toshikazu Ito, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/819,982

(22) Filed: Mar. 29, 2001

(65) Prior Publication Data

US 2001/0025810 A1 Oct. 4, 2001

(30) Foreign Application Priority Data

Mar. 30, 2000 (JP) ........................................ 2000-092651

(51) Int. Cl.[7] .............................................. B01D 15/08
(52) U.S. Cl. .................. 210/103; 73/61.56; 210/198.2; 210/101; 417/3; 417/14; 422/70
(58) Field of Search ................................ 210/101, 103, 210/143, 198.2, 416.1, 511.1, 634, 656, 659; 422/69, 70, 105; 417/1, 3–5, 14, 43; 436/161; 73/61, 56

(56) References Cited

U.S. PATENT DOCUMENTS

| | | | | |
|---|---|---|---|---|
| 4,869,374 A | * | 9/1989 | Allington ................. | 210/198.2 |
| 5,040,126 A | * | 8/1991 | Allington ................. | 210/659 |
| 5,087,360 A | * | 2/1992 | Wright et al. .............. | 210/634 |
| 5,253,981 A | * | 10/1993 | Yang et al. ................ | 417/3 |
| 5,630,706 A | * | 5/1997 | Yang ....................... | 417/3 |
| 5,866,004 A | * | 2/1999 | Houck et al. .............. | 210/634 |
| 5,897,781 A | * | 4/1999 | Dourdeville ............... | 210/656 |

* cited by examiner

Primary Examiner—Joseph W. Drodge
(74) Attorney, Agent, or Firm—Kanesaka & Takeuchi

(57) ABSTRACT

An operation portion reads an analyzing time and an analyzing flow rate from a storing portion for a next analysis to calculate a liquid delivery quantity per analysis for the next analysis, and transmits the liquid delivery quantity per analysis to a comparison portion. The comparison portion compares a pump capacity and the liquid delivery quantity per analysis, and when the comparison portion determines that the pump capacity is larger than the liquid delivery quantity per analysis, a control portion allows a mobile phase in the next analysis to be delivered by only one cycle discharging operation in a low flow rate mode. Thus, in a micro-liquid chromatography, influence of a pulsating flow can be suppressed.

6 Claims, 5 Drawing Sheets

LIQUID CHROMATOGRAPH

BACKGROUND OF THE INVENTION AND RELATED ART STATEMENT

The invention relates to a liquid chromatograph, more particularly, to a liquid chromatograph, which may be applied to a micro liquid chromatography wherein a mobile phase is delivered at a low flow rate in the order of, for example, 1–5 micro-liters/minute.

The micro liquid chromatography is used in a liquid chromatograph/mass spectrometer (LC/MS) and an analysis of a micro sample of protein or peptide, an absolute quantity of which is limited.

As a liquid delivery mechanism of a liquid chromatograph, there has been proposed a plunger reciprocating type liquid delivery pump for delivering a mobile phase through a reciprocating movement of a plunger. In the plunger reciprocating type liquid delivery pump, the plunger is reciprocated in a pump head by using a mechanism for converting a rotating movement of a driving motor into a linear movement. The mobile phase is sucked into the pump head by the reciprocating movement of the plunger and actions of a check valve or a flow line selecting valve provided on a liquid entrance side and a liquid exit side of the pump head, respectively, and then is discharged to a column side from a sample injection portion.

As the plunger reciprocating type liquid delivery pump as described above, there have been proposed a single plunger type pump formed of one set of the plunger and the pump head, and a double plunger type pump including two sets of the plungers and pump heads disposed in parallel or in series.

In the plunger reciprocating type liquid delivery pump, a liquid is delivered by repeating discharging and sucking operations by reciprocating the plunger. An operation cycle of a liquid delivery pump to be used in a normal liquid chromatograph is independent, not in synchronism with an analyzing time or an analyzing cycle, regardless of the analyzing time or the analyzing cycle.

In the single plunger type pump, since the liquid is delivered through repetition of the discharging operation and the quick sucking operation of the plunger, a pulsating flow is generated every cycle of the plunger reciprocating movement. In the double plunger type pump, also, the pulsating flow is generated due to shifting of the discharging operation and sucking operation of the two plungers in both parallel-type and a series-type.

Also, as an example of the liquid chromatography, there has been known a micro liquid chromatography for analyzing at a low flow rate in the order of, for example, 1–5 micro-liters/minute, by micrifying a separation column and a flow line. The micro liquid chromatography can be sensitized by suppressing diffusion of a sample, and allows the performance of the liquid chromatograph/mass spectrometer requiring carburation of the mobile phase containing separation components, to be maximized.

The pulsating flow appears as a noise of a detector base line, which may cause a bad influence in analyzing the results. Especially, in the micro liquid chromatography where the analysis is carried out at a low flow rate, the bad influence to the analyzing results by the pulsating flow is large.

The present invention has been made to solve the above problems, and an object of the invention is to provide a liquid chromatograph, wherein in case the liquid chromatograph is applied to the micro liquid chromatography, the influence of the pulsating flow to the analyzing result is suppressed.

Further objects and advantages of the invention will be apparent from the following description of the invention.

SUMMARY OF THE INVENTION

A liquid chromatograph of the invention is basically formed of a liquid delivery mechanism having a pump with a plunger for delivering a liquid or mobile phase through a reciprocating movement of the plunger, a storing portion for storing each predetermined analyzing time and analyzing flow rate set beforehand, an operation portion electrically connected to the storing portion for calculating a liquid delivery quantity per analysis for an analysis to be performed or next analysis based on the analyzing time and the analyzing flow rate for the next analysis, a comparison portion electrically connected to the operation portion for comparing a pump capacity and the liquid delivery quantity for the next analysis, and a control portion electrically connected to the comparison portion and the liquid delivery mechanism for controlling a liquid transfer operation by the liquid delivery mechanism. When the comparison portion determines that the pump capacity is larger than the liquid delivery quantity for the next analysis, the control portion controls the liquid delivery mechanism to perform a low-flow rate liquid delivery mode where the liquid is delivered by only one cycle discharging operation of the pump during the analysis to be performed. Accordingly, influence by a pulsation flow from the pump is avoided in the analysis.

DETAILED DESCRIPTION OF PREFERRED EMBODIMENTS

Figure 1:
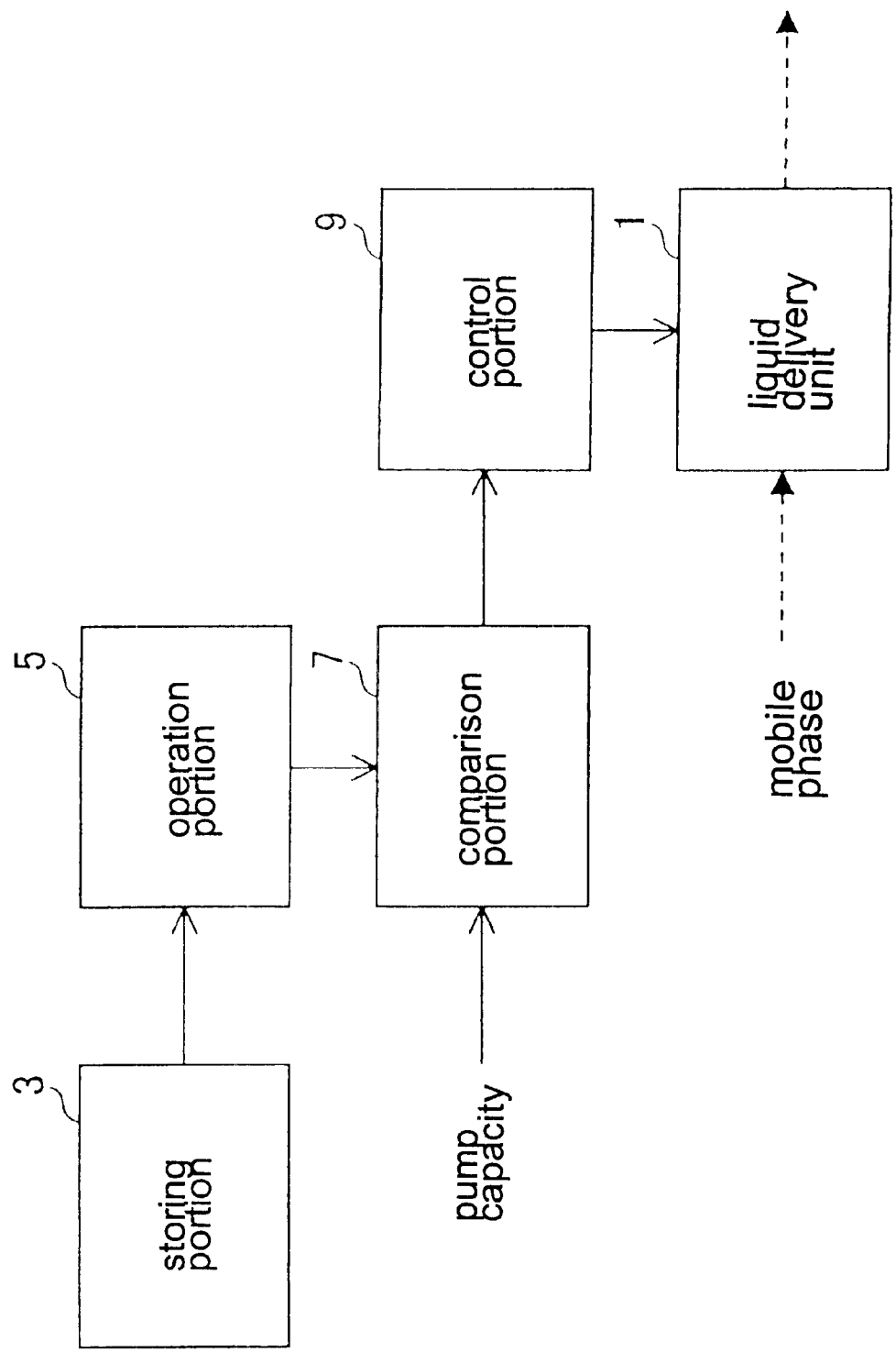
FIG. 1 is a block diagram showing an embodiment according to the present invention.

FIG. 1 is a block diagram of a liquid chromatograph according to the present invention. A liquid chromatograph of the present invention includes a liquid delivery mechanism or unit 1 provided with a pump for delivering a liquid through reciprocating movements of a plunger; a storing portion 3 for storing a predetermined analyzing time and a predetermined analyzing flow rate as analyzing conditions in each analysis; and a control portion 9 for controlling a liquid delivery operation by the liquid delivery mechanism 1. The liquid chromatograph further includes a calculating or operation portion 5 for calculating a total liquid delivery quantity, i.e. using amount, per analysis for a next analysis based on an analyzing time and analyzing flow quantity for the next analysis stored in the storing portion 3; and a comparison portion 7 for comparing a pump capacity and the total liquid delivery quantity per analysis. When the comparison portion 7 determines that the pump. capacity is larger than the total liquid delivery quantity per analysis, the control portion 9 controls to deliver the liquid in a low flow rate liquid delivery mode by only one discharging operation cycle of the pump during the next analysis.

Figure 2:
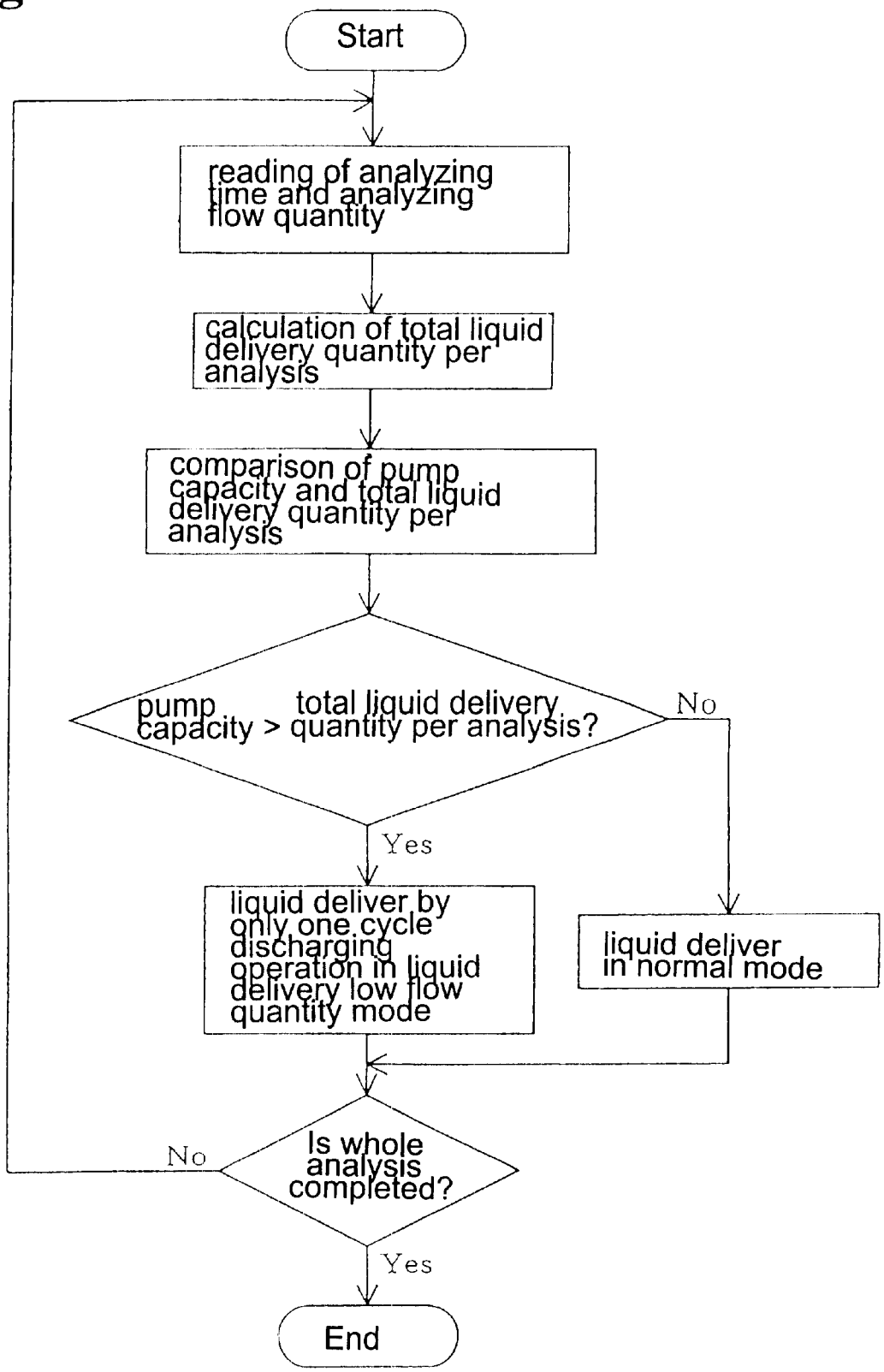
FIG. 2 is a flow chart showing an example of an operation of the present invention.

FIG. 2 is a flow chart showing an example of operation of the present invention. The operation portion 5 reads an analyzing time and an analyzing flow quantity, i.e. using amount, for the next analysis from the storing portion 3 to calculate a total liquid delivery quantity, i.e. using amount, per analysis for the next analysis, and transmits it to the comparison portion 7. The comparison portion 7 compares the pump capacity and the total liquid delivery quantity per analysis from the operation portion 5. The pump capacity may be stored in the storing portion 3 or in other storing device.

In the micro liquid chromatography, a liquid may be delivered at a low flow rate in the order of, for example, 1–5 micro-liters/minute with respect to a pump capacity of 100 micro-liters, i.e. the pump capacity is larger than the total liquid delivery quantity, i.e. using amount, per analysis.

In such a case, when the comparison portion 7 determines that the pump capacity is larger than the total liquid delivery quantity per analysis, the control portion 9 controls to deliver the liquid in the low flow rate liquid delivery mode by only one cycle of the discharging operation of the pump during the next analysis. Thus, an influence exerted on the analyzing results by a pulsating flow of the mobile phase liquid in the micro liquid chromatography can be suppressed.

In case the comparison portion 7 determines that the pump capacity is smaller than the total liquid delivery quantity per analysis, the control portion 9 controls to deliver the liquid in a normal liquid delivery mode through a sucking operation and a discharging operation by the reciprocating movements of the plunger.

In the flow chart shown in FIG. 2, although the pump capacity and the total liquid delivery quantity per analysis for the next analysis are compared every analysis, in case a plurality of analyses stored in the storing portion 3 is repeated with the same analyzing time and analyzing flow rate, comparison of the total liquid delivery quantity per analysis for the next analysis and the pump capacity may be omitted.

Also, it is preferable that either the normal liquid delivery mode or the low flow rate liquid delivery mode for the next analysis is selected before the current analysis is completed.

It is preferable that in case the pump includes a plurality of pump heads independently controlled by respective plungers, when the comparison portion 7 determines that the pump capacity of the pump head is larger than the total liquid delivery quantity per analysis, the control portion 9 controls to change the pump head every analysis, and allows at least the total liquid delivery quantity per analysis of the mobile phase to be sucked in the pump head to be used in the next analysis before the next analysis starts, so that the next analysis is carried out through the liquid delivery in the low flow rate liquid delivery mode by the other pump head.

As a result, the influence of the pulsating flow during the next analysis can be suppressed. Further, by allowing at least the total liquid delivery quantity per analysis of the mobile phase to be sucked into another pump head different from the pump head in the discharging operation at the time of termination of the current analysis, the next analysis can be started immediately after the current analysis is completed.

In case the pump includes a single pump head, when the comparison portion 7 determines that the pump capacity of the pump head is larger than the total liquid delivery quantity per analysis, the control portion 9 allows at least the total liquid delivery quantity per analysis of the mobile phase to be sucked in the pump head before the next analysis starts, so that the next analysis is carried out through the liquid delivery in the low flow rate liquid delivery mode by the pump head. As a result, the influence of the pulsating flow during the next analysis can be suppressed.

It is also preferable that the operation portion 5 calculates a mobile phase remaining quantity in the pump head during the discharging operation at a starting time of the next analysis. The comparison portion 7 also compares the mobile phase remaining quantity in the pump head and the total liquid delivery quantity per analysis calculated by the operation portion 5. When the comparison portion 7 determines that the mobile phase remaining quantity in the pump head is larger than the total liquid delivery quantity per analysis, the control portion 9 allows the pump head in the discharging operation to continue, so that the next analysis is carried out in the low flow rate liquid delivery mode by the pump head.

Figure 3:
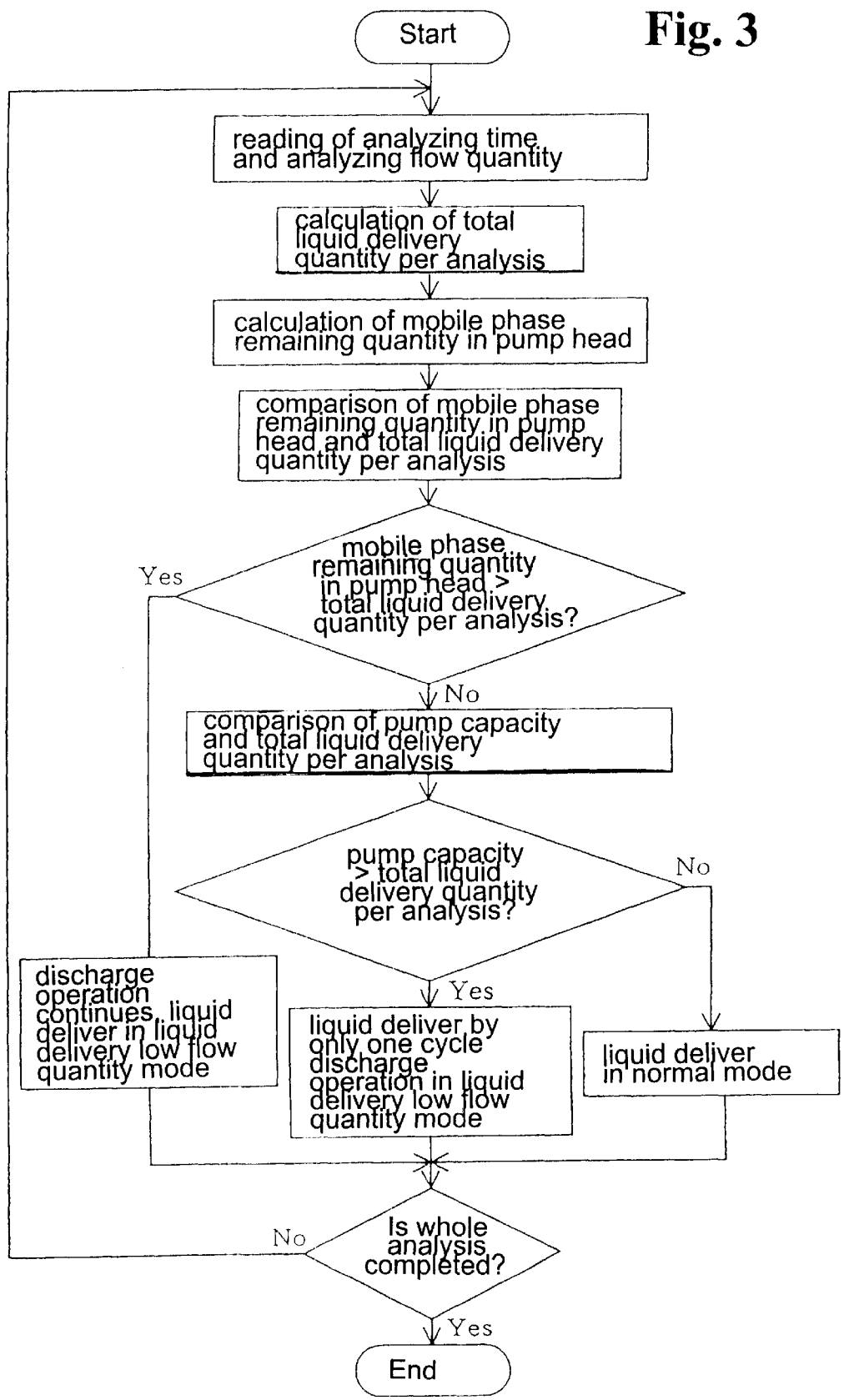
FIG. 3 is a flow chart showing another example of an operation of the present invention.

FIG. 3 is a flow chart showing another embodiment of operations of the present invention. The operation portion 5 calculates the total liquid delivery quantity per analysis for the next analysis in the same manner as in the flow chart shown in FIG. 2, and transmits it to the comparison portion 7. Further, the operation portion 5 also calculates a mobile phase remaining quantity in the pump head when the next analysis starts, and transmits it to the comparison portion 7. The comparison portion 7 compares the total liquid delivery quantity per analysis and the mobile phase remaining quantity in the pump head from the operation portion 5.

When the comparison portion 7 determines that the mobile phase remaining quantity in the pump head is larger than the total liquid delivery quantity per analysis, the control portion 9 allows the pump head in the discharging operation to continue discharging, so that the next analysis is carried out by the liquid delivery in the low flow rate liquid delivery mode by the same pump head. Thus, the influence of the pulsating flow during the next analysis can be suppressed. Further, the next analysis can be started immediately after the current analysis is completed.

When the comparison portion 7 determines that the mobile phase remaining quantity in the pump head is smaller than the total liquid delivery quantity per analysis, the comparison portion 7 further compares the pump capacity and the total liquid delivery quantity per analysis. The operations thereafter are the same as those after the comparison of the pump capacity and the total liquid delivery quantity per analysis, as shown by the flow chart in FIG. 2.

Figure 4:
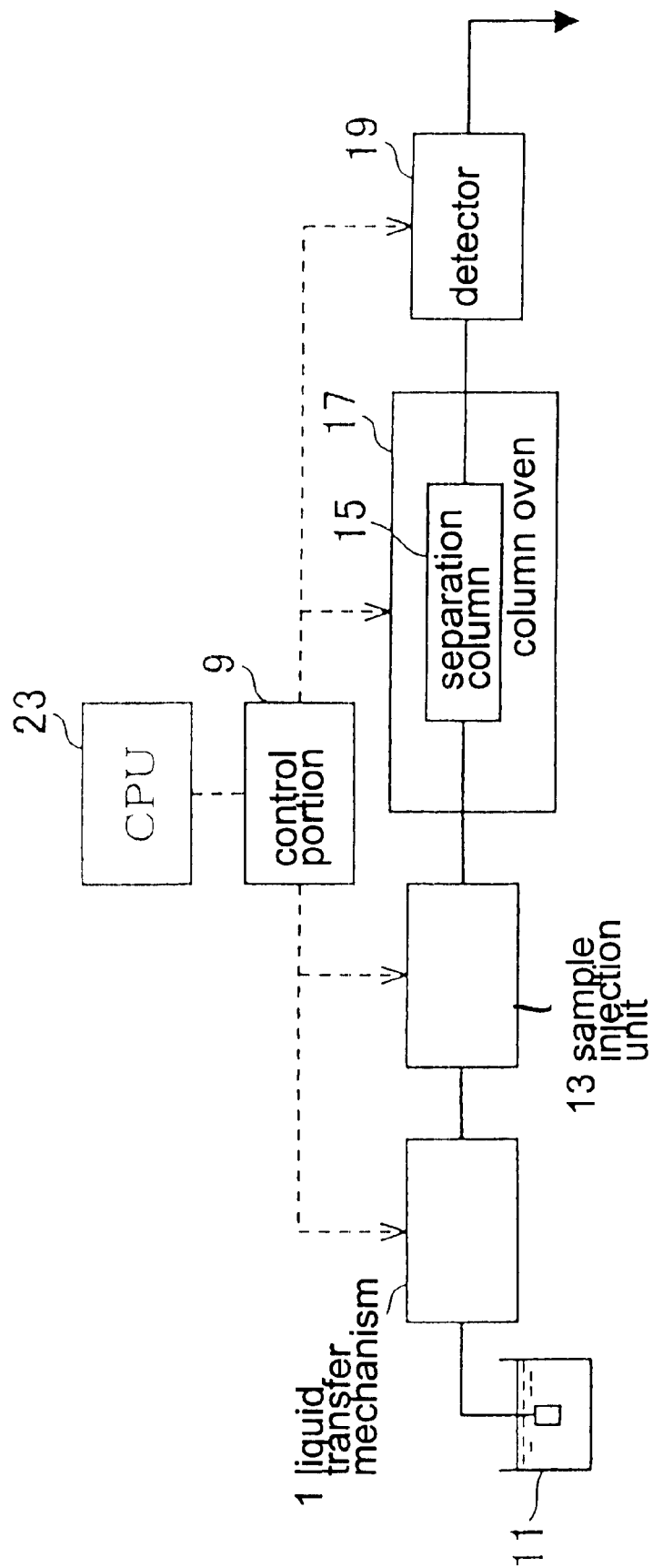
FIG. 4 is a block diagram showing an embodiment of a liquid chromatograph to which the present invention is applied.

FIG. 4 is a block diagram showing a liquid chromatograph of an embodiment according to the present invention. A mobile phase from a mobile phase bin 11 is delivered to a separation column 15 by a liquid delivery mechanism 1. A sample injection unit 13 for injecting a sample into the mobile phase is provided on a flow line located between the liquid delivery mechanism 1 and the separation column 15. The separation column 15 is housed in a column oven 17 to be held at a predetermined temperature. A detector 19 for detecting sample components separated at the separation column is provided at a flow line exit of the separation column 15.

The liquid delivery mechanism 1, sample injection unit 13, column oven 17 and detector 19 are electrically connected to a control portion 9 to control. The control portion 9 is electrically connected to a CPU 23.

The control portion 3, an operation portion 5 and a comparison portion 7 are formed by the CPU 23.

Figure 5:
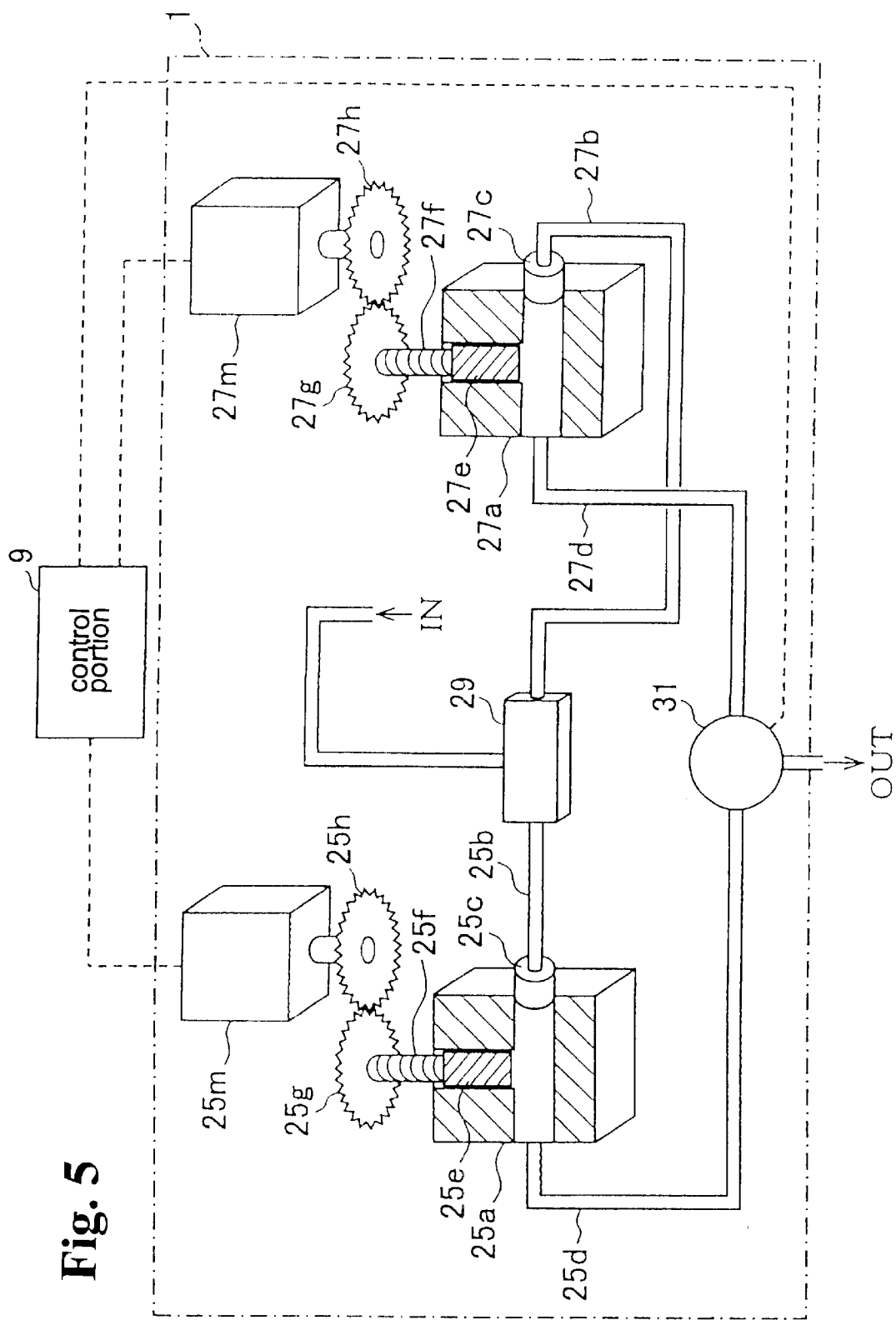
FIG. 5 is a block diagram showing an embodiment of a liquid delivery mechanism constituting the present invention.

FIG. 5 is a block diagram showing the liquid delivery mechanism 1 of an embodiment according to the present invention, wherein two pump heads 25a, 27a are disposed. Flow lines 25b, 27b on liquid entrance sides of the pump heads 25a, 27a are connected to a three-way joint 29 through check valves 25c, 27c, and further connected to the mobile phase bin 11 (which is omitted in FIG. 5) through the three-way joint 29 (refer to "IN" in the drawing). Flow lines 25d, 27d on the liquid exit sides of the pump heads 25a, 27a are connected to the sample injection unit 13 (which is omitted in FIG. 5) through a flow line selecting valve 31 (refer to "OUT" in the drawing). The flow line selecting valve 31 is electrically connected to the control portion 9, and based on the control from the control portion 9, the flow line connected to the sample injection unit 13 is shifted to the flow line 25d or 27d.

A plunger 25e is reciprocally disposed in the pump head 25a, and a plunger 27e is reciprocally disposed in the pump head 27a. Transmission screws 25f, 27f are connected to base end portions of the plungers 25e, 27e. The plungers 25e, 27e are reciprocated through rotations of the transmission screws 25f, 27f to thereby carry out discharging and sucking operations of the respective pump heads 25, 27.

Gears 25g, 27g are fixed to the screw heads of the transmission screws 25f, 27f. Gears 25h, 27h attached to rotation shafts of driving motors 25m, 27m are engaged with the gears 25g, 27g. The transmission screw 25f is rotated by the rotation of the driving motor 25m through the gears 25h, 25g, and the feed screw 27f is rotated by the rotation of the driving motor 27m through the gears 27h, 27g. The driving motors 25m, 27m are electrically connected to the control portion 9, and are mutually independently rotated by the control from the control portion 9. More specifically, the feed screws 25f, 27f are mutually independently rotated, so that the plungers 25e, 27e are mutually independently driven.

Next, operation of the liquid delivery mechanism 1 is explained. In case a liquid or mobile phase is delivered by a normal mode, discharging operations of the pump heads 25a, 27a are alternately continuously carried out, and the flow line 25d or 27d connected to the pump head 25a or 27a on a side where the discharging operation is carried out is selectively connected to a flow line connected to the sample injection mechanism 13 by the flow line selecting valve 31. The discharging operations of the pump heads 25a, 27a are carried out by using the whole strokes of the plungers 25e, 27e. Namely, when the discharge of the whole stroke of the plunger 25e or 27e is completed, by shifting the flow-path selecting valve 31, the discharging operation of the other of the plunger 25e or 27e starts. The pump head 25a or 27a on the side where the discharging operation has been completed starts a suction operation to thereby suck the mobile phase into the pump head 25a or 27a through the check valve 25c or 27c and the three-way joint 29.

In the present embodiment, the analyzing conditions for the plural analyses are set before the analyses are carried out and stored in the storing portion 3 of the CPU 23, so that the control portion 9 controls the liquid delivery mechanism 1 and sample injection unit 13 based on the set values.

With reference to FIGS. 1, 2, 4 and 5, a first example of the operation is explained. The operation portion 5 of the CPU 23 calculates a total liquid delivery quantity per analysis based on a liquid delivery flow quantity and an analyzing time per analysis stored in the storing portion 3 and transmits the total liquid delivery quantity per analysis to the comparison portion 7 of the CPU 23. The comparison portion 7 compares the total liquid delivery quantity per analysis calculated by the operation portion 5 and pump capacities of the pump heads 25a, 27a stored in the storing portion 3 or other storing device.

In case the comparison portion 7 determines that the pump capacity is larger than the total liquid delivery quantity per analysis, the control portion 9 shifts to the low flow rate mode when the next analysis starts, so that the flow line selecting valve 31 is automatically shifted in synchronism with the start of the next analysis even if the discharging operation of the pump head 25a or 27a which has been discharging is not completed to start a discharging operation of one of the pump heads 25a and 27a which has completed the sucking operation. Thus, the mobile phase is delivered by only one cycle discharging operation of the pump head 25a or 27a to carry out the analysis. The other pump head 27a or 25a which has discharged starts the sucking operation to complete the sucking operation during the analysis.

With reference to FIGS. 1, 3, 4 and 5, a second example of the operation is explained. The operation portion 5 of the CPU 23 calculates a total liquid delivery quantity per analysis based on the liquid delivery flow rate and the analyzing time per analysis stored in the storing portion 3, and further calculates a mobile phase remaining quantity in the pump head 25a or 27a in a discharging operation to thereby transmit, to the comparison portion 7 of the CPU 23, the total liquid delivery quantity per analysis and the mobile phase remaining quantity in the pump head. The comparison portion 7 compares the total liquid delivery quantity per analysis and the mobile phase remaining quantity in the pump head calculated by the operation portion 5.

In case the comparison portion 7 determines that the mobile phase remaining quantity in the pump head is larger than the total liquid delivery quantity per analysis, the control portion 9 shifts to the low flow rate mode when the next analysis starts, and allows the discharging operation of the pump head 25a or 27a in the discharging operation to continue at the time of starting the next analysis while keeping a connecting state of the flow line selecting valve 31.

In case the comparison portion 7 determines that the mobile phase remaining quantity in the pump head is smaller than the total liquid delivery quantity per analysis, in the same manner as in the first example, the comparison portion 7 compares the total liquid delivery quantity per analysis and the pump capacity of the pump heads 25a, 27a, and when the comparison portion 7 determines that the pump capacity is larger than the total liquid delivery quantity per analysis, the control portion 9 performs the next analysis at the low flow rate liquid delivery mode.

As described hereinabove, in the first and second examples of the operations, in case the total liquid delivery quantity per analysis is smaller than the mobile phase remaining quantity in the pump head or the pump capacity in the low flow rate liquid delivery, the liquid delivery mode is shifted or the flow line selecting valve 31 is shifted, or both of them are carried out, in synchronism with a completion or start of a new analysis. Thus, the influence of a pulsating flow generated when the two pump heads 25a, 27a are shifted or the discharging operation is shifted to the sucking operation, does not appear on the base line of the detector 19 during the analysis. Thus, the influence of the pulsating flow does not appear on the analyzing data.

In the present example, although the liquid delivery mechanism 1 includes the two pump heads 25a, 27a, the present invention is not limited thereto. One or more than three pump heads may be used. In case the liquid delivery mechanism 1, for example, includes a single plunger type pump, and the pump capacity is larger than the total liquid delivery quantity per analysis, even if the discharge of the whole stroke of the plunger is not completed at the time of analysis completion, the influence of the pulsating flow can be removed from the data of the analysis by shifting to start the discharging operation from a quick sucking operation in synchronism with the completion of the analysis or starting the analysis, in the same manner as in the example shown in FIGS. 4 and 5.

Also, a micro liquid chromatography to which the present invention is applied is not limited to those wherein the mobile phase is delivered at a flow rate in the order of 1–5 micro-litters/minute, and can be applied to a micro-liquid chromatography having any flow rate if the total liquid delivery quantity per analysis is smaller than the pump capacity.

In the liquid chromatograph of the present invention, the operation portion reads the analyzing time and the analyzing flow rate for the next analysis from the storing portion to calculate the total liquid delivery quantity per analysis for the next analysis, and the comparison portion compares a pump capacity and the total liquid delivery quantity per analysis from the operation portion. When the comparison portion determines that the pump capacity is larger than the total liquid delivery quantity per analysis, the control portion controls to carry out the liquid delivery by only one cycle discharging operation of the pump during the next analysis, i.e. in a low flow rate liquid delivery mode. Thus, when the present invention is applied to the micro-liquid chromatography, the liquid delivery can be carried out without influence of the pulsating flow.

In case the pump includes a plurality of pump heads where the respective plungers can be independently controlled, and when the comparison portion determines that the pump capacity of the pump head is larger than the total liquid delivery quantity per analysis, the control portion changes the pump head every analysis so that the mobile phase of, at least, the total liquid delivery quantity per analysis is sucked into the pump head to be used in the next analysis before the next analysis starts and the next analysis is carried out with the liquid delivery in the low flow rate liquid delivery mode by the pump head. Thus, the influence of the pulsating flow during the next analysis can be suppressed, and further, the next analysis can be started immediately after completion of the current analysis.

In case the pump includes a single pump head, and when the comparison portion determines that the pump capacity of the pump head is larger than the total liquid delivery quantity per analysis, at least the mobile phase of the total liquid delivery quantity per analysis is sucked into the pump head before the next analysis starts and the next analysis is carried out by the liquid delivery in the low flow rate liquid delivery mode of the pump head. Thus, the influence of the pulsating flow during the next analysis can be suppressed.

The operation portion also calculates the mobile phase remaining quantity in the pump head in the discharging operation when the next analysis starts; the comparison portion compares a mobile phase remaining quantity in the pump head and the total liquid delivery quantity per analysis calculated by the operation portion; and when the comparison portion determines that the mobile phase remaining quantity in the pump head is larger than the total liquid delivery quantity per analysis, the control portion allows the pump head in a discharging operation to continue the discharging operation. Thus, when the next analysis is carried out with liquid delivery in the low flow rate liquid delivery mode by the pump head, the influence of the pulsating flow during the next analysis can be suppressed, and further, the next analysis can be started immediately after the current analysis is completed.

While the invention has been explained with reference to the specific embodiment of the invention, the explanation is illustrative and the invention is limited only by the appended claims.

What is claimed is:

1. A liquid chromatograph comprising:
   a liquid delivery unit having a pump with a predetermined pump capacity and a plunger for delivering a liquid through a reciprocating movement of the plunger, said liquid delivery unit having a low-flow rate liquid delivery mode where the liquid is delivered by only one cycle discharging operation of the pump in one analysis and a normal liquid delivery mode by reciprocating movements of the plunger in said one analysis,
   a storing portion having therein a predetermined analyzing time and an analyzing flow rate for a next analysis to be performed, which are set beforehand,
   an operation portion electrically connected to the storing portion and calculating a liquid delivery quantity for the next analysis to be performed based on the analyzing time and the analyzing flow rate,
   a comparison portion electrically connected to the operation portion and operable for comparing the pump capacity and the liquid delivery quantity for the next analysis to be performed, and
   a control portion electrically connected to the comparison portion and the liquid delivery unit for controlling a liquid delivery operation by the liquid delivery unit, said control portion operable, when said comparison portion determines that the pump capacity is larger than the liquid delivery quantity for the next analysis to be performed, for controlling the liquid delivery unit to perform the low-flow rate liquid delivery mode.

2. A liquid chromatograph as claimed in claim 1, wherein said pump includes a plurality of pump heads having plungers and being controlled independently by said control portion, said liquid chromatograph performing a plurality of same analyses such that when the comparison portion determines that the pump capacity of each of the pump heads is larger than the liquid delivery quantity for each of the analyses to be performed, said control portion changes the pump head for each analysis to be performed and operates each of the pump heads for the analyses to suck therein at least a liquid delivery quantity for each of the analyses before each of the analyses to be performed starts so that each of the analyses to be performed is carried out through the liquid delivery in the low-flow rate liquid delivery mode by each of the pump heads.

3. A liquid chromatograph as claimed in claim 1, wherein said pump includes a single pump head with the plunger, said control portion, when the comparison portion determines that the pump capacity of the pump head is larger than the liquid delivery quantity for the next analysis to be performed, allowing the pump head to suck therein at least the liquid delivery quantity for the next analysis before the next analysis starts so that the next analysis is carried out through the liquid delivery in the low-flow rate liquid delivery mode by the pump head.

4. A liquid chromatograph as claimed in claim 1, wherein said operation portion includes means for calculating a mobile phase remaining quantity in the pump head before the next analysis starts; said comparison portion compares the mobile phase remaining quantity in the pump head calculated by the operation portion and the liquid delivery quantity for the next analysis; and when the comparison portion determines that the mobile phase remaining quantity in the pump head is larger than the liquid delivery quantity for the next analysis, the control portion allows the pump head in a discharging operation to continue discharging so that the next analysis is carried out by the liquid delivery in the low-flow rate liquid delivery mode by the pump head.

5. A liquid chromatograph as claimed in claim 1, wherein said storing portion, operation portion and comparison portion are included in a central processing unit.

6. A liquid chromatograph comprising:

a liquid delivery unit having a pump with a predetermined pump capacity and a plunger for delivering a liquid through a reciprocating movement of the plunger, said liquid delivery unit having a low-flow rate liquid delivery mode where the liquid is delivered by only one cycle discharging operation of the pump in one analysis, a storing portion having therein a predetermined analyzing time and an analyzing flow rate for a next analysis to be performed, which are set beforehand, an operation portion electrically connected to the storing portion and calculating a liquid delivery quantity for the next analysis to be performed based on the analyzing time and the analyzing flow rate, a comparison portion electrically connected to the operation portion and operable for comparing the pump capacity and the liquid delivery quantity for the next analysis to be performed, said storing portion, operation portion and comparison portion being included in a central processing unit, a control portion electrically connected to the comparison portion and the liquid delivery unit for controlling a liquid delivery operation by the liquid delivery unit, said control portion operable, when said comparison portion determines that the pump capacity is larger than the liquid delivery quantity for the next analysis to be performed, for controlling the liquid delivery unit to perform the low-flow rate liquid delivery mode, and a sample injection unit connected to a line from the liquid delivery unit for injecting a sample into the liquid from the liquid delivery unit, a separation column for separating components of the sample, a column oven for housing the separation column, and a detector connected to the separation column for detecting sample components separated at the separation column, said liquid delivery unit, sample injection unit, column oven and detector being electrically connected to the control portion which is electrically connected to the central processing unit.

* * * * *